(12) United States Patent
Horie (10) Patent No.: US 7,393,102 B2
(45) Date of Patent: Jul. 1, 2008

(54) EYESIGHT IMPROVING DEVICE

(76) Inventor: Hidenori Horie, 3-2-12, Mutsuuraminami, Kanazawa-ku, Yokohama-shi, Kanagawa 236-0038 (JP)

( * ) Notice: Subject to any disclaimer, the term of this patent is extended or adjusted under 35 U.S.C. 154(b) by 195 days.

(21) Appl. No.: 10/541,662

(22) PCT Filed: Jan. 16, 2004

(86) PCT No.: PCT/JP2004/000289

§ 371 (c)(1),
(2), (4) Date: Jul. 8, 2005

(87) PCT Pub. No.: WO2004/066900

PCT Pub. Date: Aug. 12, 2004

(65) Prior Publication Data

US 2006/0103808 A1  May 18, 2006

(30) Foreign Application Priority Data

Jan. 16, 2003  (JP)  ............................. 2003-008103

(51) Int. Cl.
*A61B 3/14* (2006.01)
*A61B 3/00* (2006.01)
(52) U.S. Cl. ........................ 351/208; 351/200
(58) Field of Classification Search ................. 351/208, 351/211
See application file for complete search history.

(56) References Cited

U.S. PATENT DOCUMENTS 4,105,302 A * 8/1978 Tate, Jr. ........................ 351/210
4,408,846 A * 10/1983 Balliet ........................ 351/203
5,237,351 A * 8/1993 Kohayakawa et al. ........ 351/243

FOREIGN PATENT DOCUMENTS

| JP | U 62-142326 | 9/1987 |
| JP | A-06-133257 | 5/1994 |
| JP | A 06-339501 | 12/1994 |

(Continued)

OTHER PUBLICATIONS

Tokoro et al.; "Modern Textbook of Ophthalmology"; 7th Edition; Kanehara & Co., Ltd.; 1999; pp. 36-41 and 54-68; with partial translation.

*Primary Examiner*—Jordan M. Schwartz
*Assistant Examiner*—James C Jones
(74) *Attorney, Agent, or Firm*—Oliff & Berridge, PLC (57) ABSTRACT

This patent provides an eyesight improving device which improves ocular imaging adjustment functions and is easy to use. A user puts the eyes on eyepiece parts 10, and sees a figure displayed on a target 12 by both eyes or one eye by opening or closing blocking device 14. In a state where the user focuses the eye on the figure, the target 12 is moved from a far point to a near point by target movement device 18 and is next moved from the near point to the far point, and this is repeated. In this case, the size of the figure is controlled to be changed in proportion to the distance between the eyepiece-part 10 and the target 12. The user can easily concentrate to focus the eye on the figure during the movement of the target 12. This training activates the ocular imaging adjustment functions of a ciliary muscle, a pupil, vergences and the like resulting with their improvement.

15 Claims, 9 Drawing Sheets

FOREIGN PATENT DOCUMENTS

| | | |
|---|---|---|
| JP | A 07-51333 | 2/1995 |
| JP | A-08-243137 | 9/1996 |
| JP | A-08-257077 | 10/1996 |
| JP | A 08-257078 | 10/1996 |
| JP | A 09-47479 | 2/1997 |
| JP | A-10-221639 | 8/1998 |
| JP | A-11-238124 | 8/1999 |
| JP | A-2000-070317 | 3/2000 |
| JP | A 2000-116600 | 4/2000 |
| JP | A 2002-336317 | 11/2002 |
| JP | A-2003-334221 | 11/2003 |
| WO | WO 02/091983 A1 | 11/2002 |

* cited by examiner

EYESIGHT IMPROVING DEVICE

TECHNICAL FIELD

The present invention relates to an eyesight improving device, and particularly to an eyesight improving device for false myopia and presbyopia.

BACKGROUND ART

Figure 6A:
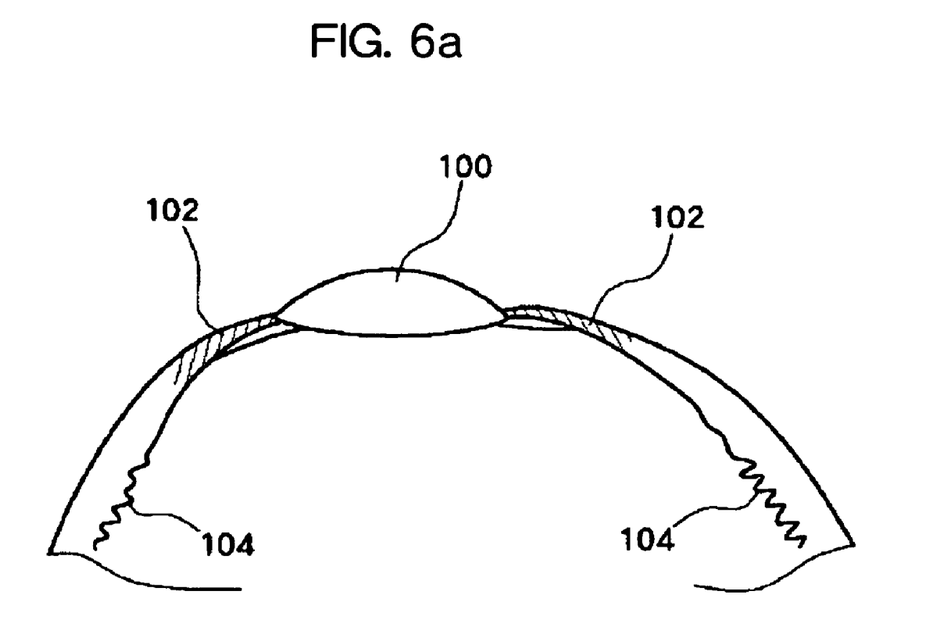
FIG. 6a is a partial sectional view of a rough structure of a human eye.
Figure 6B:
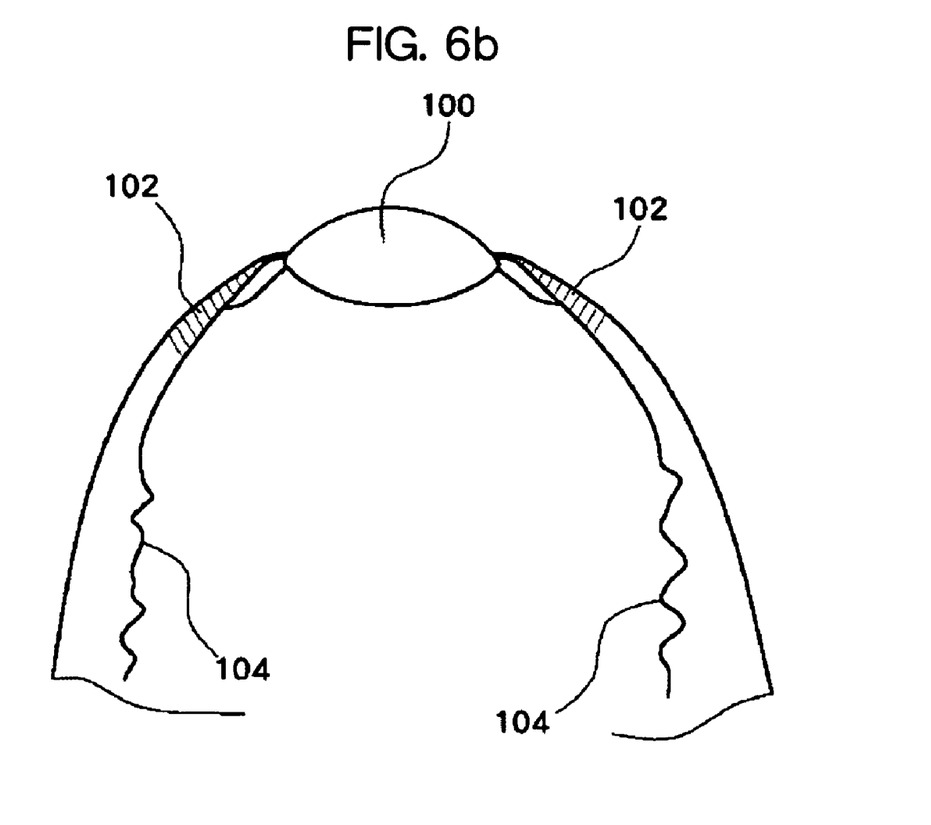
FIG. 6b is a partial sectional view of a rough structure of a human eye.

FIGS. 6a and 6b are partial sectional views of a rough structure of a human eye. FIG. 6a is a view when a far point is seen, in which since a ciliary muscle (circular muscle) 102 is relaxed, a lens 100 is pulled by the tensile force of a choroid 104, its thickness becomes thin, and its curvature becomes small. On the other hand, FIG. 6b is a view when a near point is seen, in which the tensile force of the choroid 104 to extend the lens 100 is relieved by the contraction of the ciliary muscle (circular muscle) 102, the lens 100 swells by its own elasticity, the thickness becomes thick, and the curvature becomes large. By the mechanism as stated above, the curvature (focal distance) of the lens 100 is adjusted according to the distance from an object which is seen by the eye, and the object can be clearly sensed. Further, in order to more clearly sense the object, the iris (see FIG. 8) is used to adjust the diameter of the pupil, the angle composed by binocular visual lines is adjusted according to the distance from the object, and convergence (inward movement) and divergence (outward movement) is performed.

Incidentally, the far point is an external point, an image of which is formed on the fovea centralis of the retina when no adjustment of thickness of the lens 100 is made. Besides, the near point is an external point, an image of which is formed on the fovea centralis of the retina when the adjustment of thickness of the lens 100 is extremely made.

In recent years, children start to watch from an early age a television (TV), a TV game, a personal computer or the like for a long time resulting with increase of myopia children. Some causes of the myopia are generally known, and for example, it is regarded as one cause that when time for watching an object at the near point becomes long, the contraction state of the foregoing ciliary muscle 102 becomes long, the state in which the curvature of the lens 100 is large (the lens becomes thick) continues long, and the visual axis (distance from the lens 100 to the retina) becomes long.

Besides, although there are variations among individuals, from the age of approximately 40 years, the near point moves away, and presbyopia in which a near object can not be clearly sensed progresses. It is regarded that one of the main causes is the weakening of the ciliary muscle 102.

Incidentally, non-patent document, Modern Textbook of Ophthalmology (GENDAI NO GANKAGAKU) the seventh edition, Takashi Tokoro, Jun Kanai, Kanehara & Co., Ltd. also describes the cause of myopia and presbyopia.

Conventionally, an apparatus for restoring vision decreased due to the myopia or the like is proposed. For example, patent document JP-A-6-339501 discloses a vision restoration apparatus in which a gaze plate on which a mark is displayed is reciprocated, and a user gazes at the approaching and retreating mark, so that the training of the eyes is performed.

However, in the conventional vision restoration apparatus, since the size of the mark displayed on the gaze plate is constant, there has been a problem that especially when the mark approaches the user, it is hard to bring the mark into focus, and it becomes difficult to clearly see it. It is considered that this is because when the mark approaches the user, the size of the image of the mark formed on the retina of the eye of the user watching the mark becomes large, the amount of information sent to the brain increases, and it becomes difficult to control the ocular imaging adjustment functions of the ciliary muscle 102 and the like.

The invention has been made in view of the above conventional problems, and its object is to provide an eyesight improving device which improves ocular imaging adjustment functions and is easy to use.

DISCLOSURE OF THE INVENTION

In order to achieve the above object, the invention is an eyesight improving device comprising an eyepiece part, a target visually seen from the eyepiece part and capable of displaying a suitable figure, target movement device which moves the target at a suitable speed between a far point and a near point each of which is positioned at a specified distance from the eyepiece part, and display control device which changes a size of the figure displayed on the target in proportion to a distance between the target and the eyepiece part.

The above structure enables the size of the figures to change in proportion to the distance between the target and the eyepiece part, when the target is moved. This makes it easy to focus the eye on the figure.

Besides, in the eyesight improving device, two such eyepiece parts are provided, and blocking device which blocks visual identification of the target is provided for each of them.

According to the above structure, when the eyesight improving device is used, binocular vision and monocular vision can be easily selected.

Besides, in the eyesight improving device, the target includes electric display which displays the figure visually seen from the eyepiece part.

According to the above structure, when the eyesight improving device is used, the number of selectable figures can be increased, and a clearer figure can be provided.

Besides, in the eyesight improving device, the target movement device moves the target by driving device.

According to the above structure, the movement of the target can be facilitated. Besides, since the target can be moved at an accurate speed, the vision improvement effect can be further raised.

Besides, in the eyesight improving device, the driving device can change the movement speed of the target stepwise or continuously.

According to the above structure, the movement speed most suitable for the user can be easily set.

Besides, in the eyesight improving device, the eyepiece part includes a convex lens.

Besides, in the eyesight improving device, the target is directed in the same direction as the eyepiece part, reflecting device facing the target and the eyepiece part and reflecting device movement device which moves the reflecting device at a suitable speed between two specified points, instead of the target movement device, are provided, and light from the target is reflected by the reflecting device and is incident on the eyepiece part.

According to the above respective structures, the eyesight improving device can be miniaturized.

Besides, an eyesight improving device, comprising electric display which can display a suitable figure, distance measurement device which measures a distance from a user, and display control device which changes a size of the figure displayed on the electric display in proportion to the distance from the user.

According to the structure, the small and simple eyesight improving device having a function and a form similar to a cellular phone can be realized, and can also be realized by incorporating its function in a cellular phone.

Besides, in the eyesight improving device, the figure is displayed in one of red, green and blue, and a background of the figure is black.

According to the structure, the eyesight improving device in which the user can easily concentrate on the figure can be realized.

Besides, in the eyesight improving device, the figure is ring-shaped.

Besides, in the eyesight improving device, the figure has such a size that when a distance from the eyepiece part is 25 cm, a maximum diameter is 1 cm or less. It is preferable that this figure has a shape of a capital G in alphabet.

Besides, in the eyesight improving device, the figure is displayed in white, and the background of the figure is black.

According to the above respective structures, the figure of the ring shape, the small capital G in the alphabet or the like is properly used according to a condition such as the age of the user, so that suitable vision restoration training can be carried out.

BEST MODE FOR CARRYING OUT THE INVENTION

Hereinafter, best modes of the invention will be described with reference to the drawings.

Figure 1:
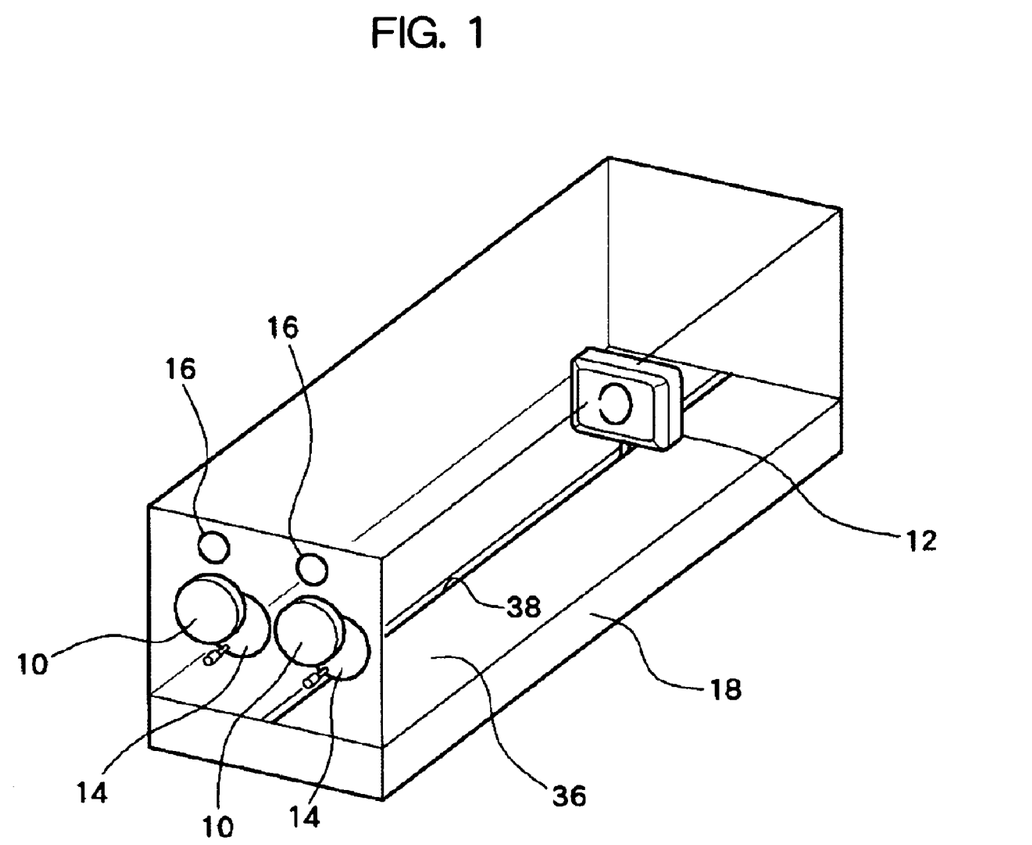
FIG. 1 is a perspective view of an eyesight improving device of the invention.

FIG. 1 is a perspective view of an eyesight improving device of the invention. Incidentally, in FIG. 1, in order to make an inner structure discernible, it is seen through wall surfaces of the apparatus. In FIG. 1, an eyepiece part 10 is provided on one of the wall surfaces, and a target 12 is disposed at a position where it can be visually seen from the eyepiece part 10. The eyepiece part 10 is such that the user puts an eye thereon and sees the target 12 therethrough, and at least one, preferably two eyepiece parts are provided. Besides, the eyepiece part 10 includes blocking device 14 which blocks visual identification of the target 12, and in the structure in which the two eyepiece parts 10 are provided, the target 12 can be visually seen by only one eye. That is, when the two blocking device 14 are opened, the target 12 can be visually seen by both eyes, and when one of the blocking device 14 is closed, the target 12 can be visually seen by the eye put on the eyepiece part 10 in which it is not closed. The opening and closing of the blocking device 14 may be realized by moving a plate-like blocking member by a manual knob, or may be realized by using an automatic shutter mechanism. Incidentally, although a transparent flat glass is used for the eyepiece part 10, a convex lens can also be used as described later.

The target 12 has such a structure that a suitable figure visually seen from the eyepiece part 10 can be displayed. It is preferably constructed of electric display such as, for example, a liquid crystal display, a CRT (cathode-ray tube) display, or a display using a light emitting element. By the electric display, it becomes possible to perform control of the size of the figure, coloring and the like, and the eyesight improving device which is easier to use can be provided. Besides, as the figure displayed on the target 12, there are various characters, symbols, pictures and the like. These figures are not particularly limited, and arbitrary ones may be used as long as they are easily visually seen from the eyepiece part 10, and the user can easily focus the eye thereon or easily confirm whether they are in focus. Incidentally, it is preferable to provide illumination device 16 so that the figure displayed on the target 12 is easy to see.

The target 12 can be moved at a suitable speed by target movement device 18 between a far point and a near point each of which is positioned at a specified distance from the eyepiece part 10. As described above, the far point and the near point are the external points, the images of which are formed on the fovea centralis of the retina when no adjustment of thickness of the lens 100 of the eye is made and when the adjustment of thickness of the leans 100 is extremely made, respectively. The target movement device 18 will be described later.

The user puts eyes on the eyepiece parts 10, opens or closes the blocking device 14, and sees the figure displayed on the target 12 by both the eyes or the one eye. At this time, the user makes an effort to clearly see the figure and focuses the eye thereon. In a state where the eye is focused on the figure as stated above, the target 12 is moved by the target movement device 18 from the far point to the near point and is next moved from the near point to the far point, and this is repeated. The user makes an effort to focus the eye on the figure also during the movement of the target 12, so that the ocular imaging adjustment functions of the ciliary muscle 102, the pupil, the convergence and divergence, and the like can be operated, and the imaging adjustment functions can be improved. By this, it becomes possible to clearly see a far object in the case of the myopia, and a near object in the case of the presbyopia, which have been difficult to clearly see. As stated above, the curvature control tissue for the leans 100, such as the ciliary muscle 102, is moved, and the adjustment of the pupil diameter, and the convergence and divergence are performed, so that the movement of the whole eyeball including the retina can be performed, and the function of the eye can be activated. Incidentally, with respect to the movement of the target 12 between the far point and the near point, in order to prevent dry eye, it is preferable that approximately 20 reciprocating motions are made one set, and while a rest is taken, two to three sets are performed twice a day.

Incidentally, after the display of a personal computer is seen for a long time, or a book or the like is read for a long time, the function of the eye can be restored by using this apparatus to perform the movement of the ciliary muscle, the pupil adjustment, and the convergence and divergence.

Figure 2A:
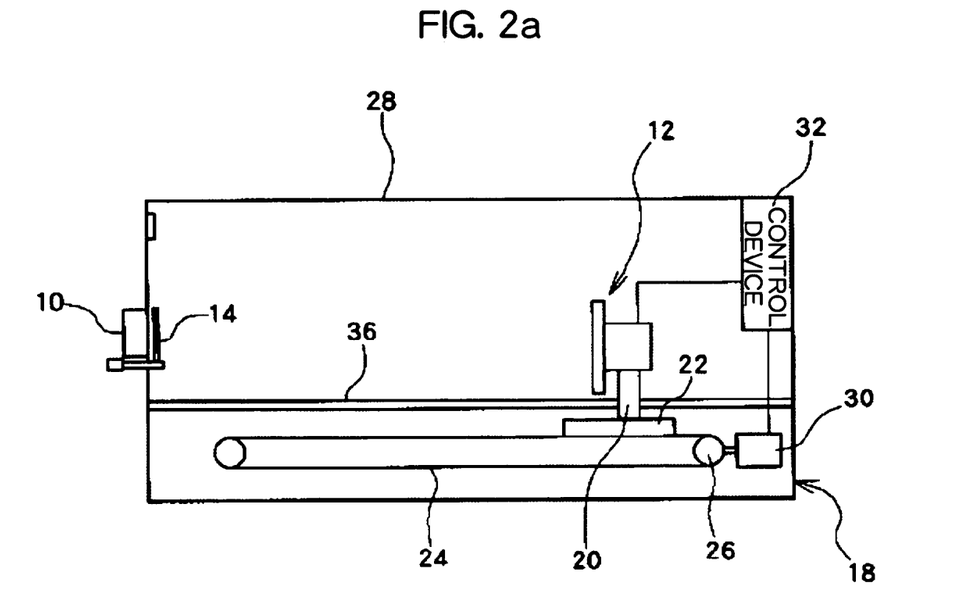
FIG. 2a is a sectional view of an embodiment of the eyesight improving device shown in FIG. 1.

FIG. 2a is a sectional view of an example of the eyesight improving device of the embodiment shown in FIG. 1. In FIG. 2a, the target 12 is fixed to a pedestal 22 by suitable support device 20 such as a post. The pedestal 22 is mounted on transport device 24 constructed of a pulley 26, a belt and the like. The pulley 26 is driven by a motor 30 to move the target 12. The motor 30 corresponds to driving device of the invention. Besides, the pedestal 22, the transport device 24, and the motor 30 constitute the target movement device 18 of the invention. In this case, the target movement device 18 may be covered by a floor 36, and the target 12 and the pedestal 22 may be coupled by the support device 20 through a gap 38 having a thin and long shape formed in the floor 36 and shown in FIG. 1. By the structure as stated above, the target 12 can be moved between the far point and the near point. Incidentally, the eyesight improving device of this embodiment may be contained in a housing 28.

Figure 2B:
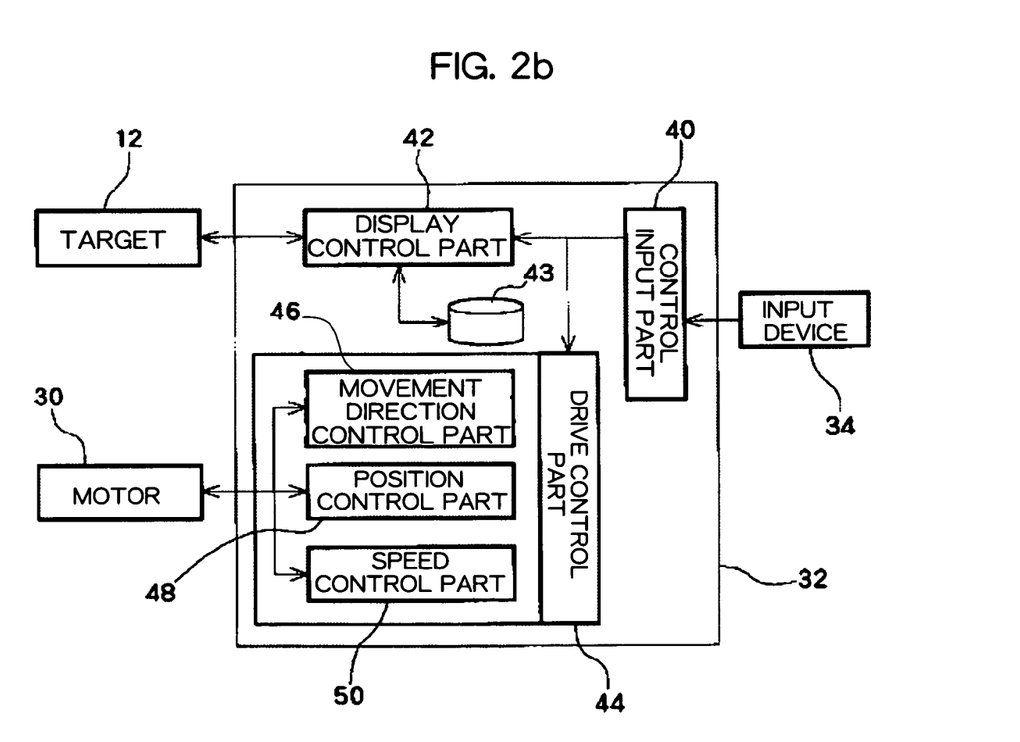
FIG. 2b is a sectional view of an embodiment of the eyesight improving device shown in FIG. 1.

The operations of the motor 30 as the driving device and the target 12 as the electric display are controlled by control device 32. FIG. 2b is a block diagram of a structure of the control device 32. In FIG. 2b, the user input control information of the eyesight improving device from input device 34 such as a keyboard, a pointing device on a display, or an input switch. The control information is received by a control input part 40, the control information relating to the figure to be displayed on the target 12 as the electric display is inputted to a display control part 42, and the control information relating to the motor 30 as the driving device is inputted to a drive control part 44. Incidentally, the input device 34 is constructed so that the user can keep it handy to use.

In the drive control part 44, a movement direction control part 46 controls whether the target 12 is moved from the far point to the near point or from the near point to the far point, a position control part 48 controls the position of the target 12, and sets the far point and the near point, and a speed control part 50 controls the movement speed of the target 12.

When a start signal of the eyesight improving device is inputted from the input device 34, the movement direction control part 46 controls the movement direction at the time when the operation is repeated in which the target 12 is moved from the far point to the near point and is next moved from the near point to the far point. Incidentally, the movement direction at the time when the start signal is inputted becomes the direction toward the near point when the target 12 is positioned at the far point at that time, and becomes the direction toward the far point when it is positioned at the near point. Besides, when the target 12 is positioned between the far point and the near point, the movement direction control part 46 selects one of the directions, however, default setting may be previously made.

Although the position control part 48 sets the positions of the far point and the near point as the distances from the eyepiece part 10, since there is a difference in the far point and the near point among individuals, it is necessary to make an adjustment for each user. Thus, the structure is made such that the far point can be controlled in the range of 500 to 1000 mm from the eyepiece part 10, and the near point can be controlled in the range of 100 to 200 mm from the eyepiece part 10. These values are inputted by the user from the input device 34. Besides, the distance from the eyepiece part 10 to the target 12 is obtained by the position control part 48 by a suitable method such as the number of revolutions of the motor. Incidentally, the distance from the eyepiece part 10 to the target 12 is inputted also to the display control part 42.

The speed control part 50 controls the movement speed of the target 12, both the structure in which the movement speed can be changed stepwise and the structure in which the movement speed is changed continuously are desirable. In the case of the structure in which the movement speed can be changed stepwise, the user can select a movement speed most suitable for himself or herself from movements speeds of, for example, 10 mm/second, 20 mm/second, 40 mm/second, 80 mm/second, 160 mm/second and 250 mm/second. By this, vision improvement can be effectively performed. Besides, in the case of the structure in which the movement speed can be continuously changed, the user can make a delicate adjustment of the movement speed most suitable for himself or herself, and the eyesight improving device which is further easy to use can be obtained. These values of the movement speed are inputted by the user from the input device 34.

The respective control outputs of the movement direction control part 46, the position control part 48, and the speed control part 50 are inputted to the motor 30 as the driving device, and specified control is performed. Incidentally, when the respective controls of the movement direction control part 46, the position control part 48, and the speed control part 50 are combined, and tiny to-and-fro vibrations are added at the time of the movement of the target 12, the user can easily focus his/her own eye on the figure displayed on the target 12, and at the same time, it becomes easy to judge whether the figure is in focus.

The control information relating to the display figure inputted from the input device 34 is inputted to the display control part 42 through the control input part 40. Besides, the distance between the eyepiece part 10 and the target 12 is also inputted from the position control part 48. In the display control part 42, based on the inputted control information, a specified figure is selected from figure data previously stored in storage device 43, and the selected figure and information relating to its size are displayed on the electric display of the target 12. Besides, the distance from the eyepiece part 10 to the target 12 is also displayed on the target 12 by the display control part 42. As stated above, the information such as the distance between the eyepiece part 10 and the target 12 and the size of the figure displayed on the target 12 is displayed on the target 12, so that it is possible to make the user grasp which figure on the target 12 can be clearly seen to what degree of distance. By this, a sense of accomplishment is given to the user, and a motivation for vision improvement efforts can be given.

Figure 3:
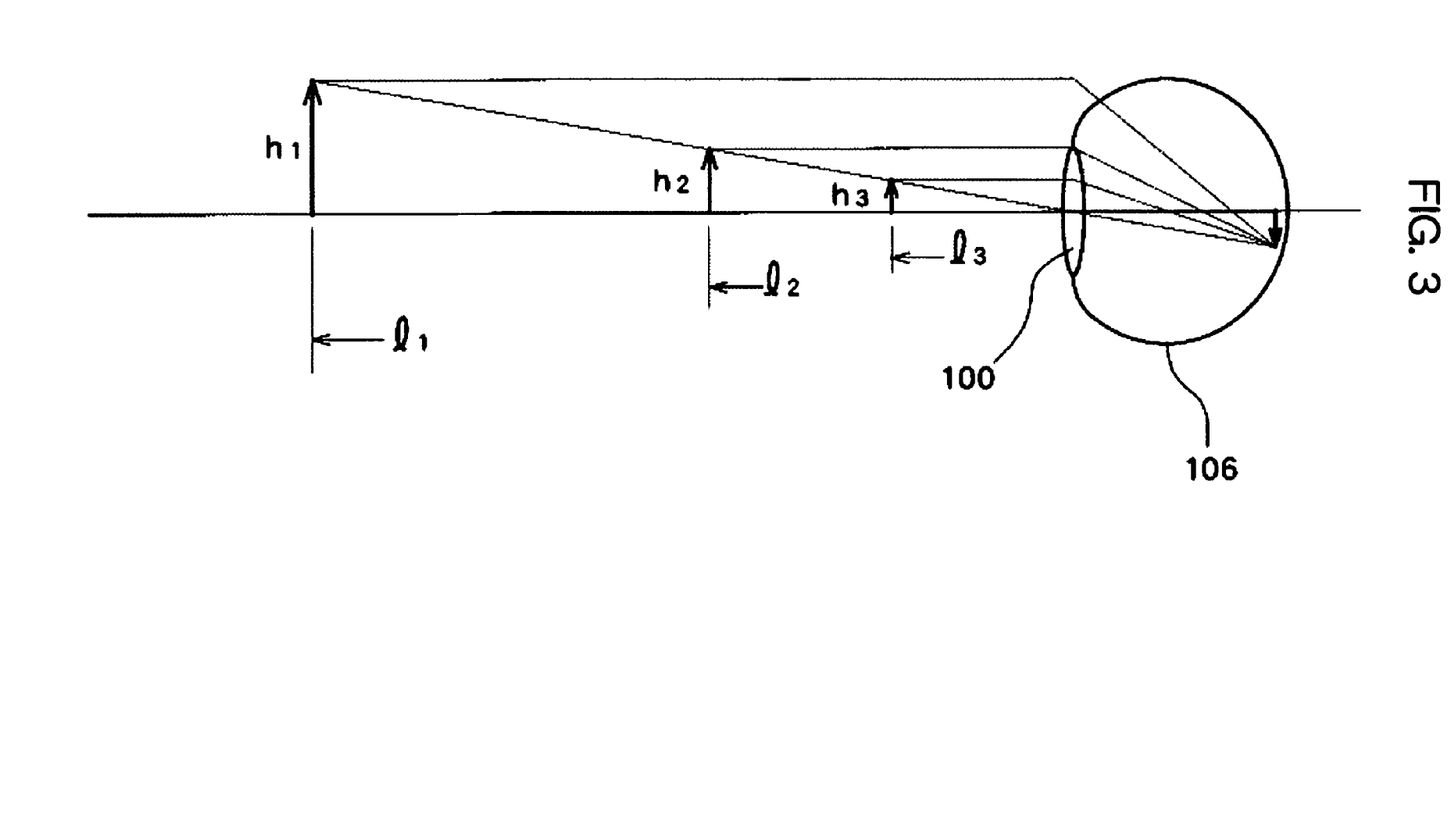
FIG. 3 is a view showing a relation between the size of a figure and the size of an image formed on the retina.

Besides, the display control part 42 performs such control that the size of the figure displayed on the target 12 is changed in proportion to the distance between the target 12 and the eyepiece part 10. FIG. 3 shows a relation between the size of the figure and the size of the image formed on the retina of the eye in the case where such control is performed. When the figure with a size $h_1$ is displayed by the target 12 at a position (for example, the far point) of a distance $l_1$ from the lens 100 of the eyeball 106 watching the target 12 from the eyepiece part 10, an image is formed on the retina by the action of the ocular imaging adjustment functions of the ciliary muscle 102 and the like. Next, when the size of the figure is decreased in proportion to the distance between the lens 100 and the figure at the time when the target 12 displaying the figure is made to approach the eye by the target movement device 18, the size of the image formed on the retina becomes constant. That is, when the figure which is watched approaches, the focal distance of the lens 100 is adjusted by the action of the ocular imaging adjustment functions so that the image of the figure is formed on the retina. Since the incident angle of light passing through the center of the lens 100 is not changed, the size of the image is kept constant. For example, when the size of the figure positioned at a distance of $l_2$ from the lens 100 is made $h_2$, and the size of the figure positioned at a distance $l_1$ from the lens 100 is made $h_3$, when the size of the figure is controlled to satisfy the relation of $l_1:l_2:l_3=h_1:h_2:h_3$, the size of the image on the retina always becomes constant. Incidentally, in the case where the target 12 is moved away from the eye, the size of the figure is increased in proportion to the distance between the lens 100 and the figure.

As stated above, when the size of the image formed on the retina of the eye is kept constant, the amount of visual information sent to the brain can be suppressed, and it becomes easy for the user to focus the eye on the figure. Thus, the eyesight improving device which is easy for the user to see and to use can be realized. This effect becomes remarkable especially when the target 12 approaches the user. This is because in the case where the target 12 approaches the user, when the size of the figure is constant, the size of the image formed on the retina becomes large, and the amount of information sent to the brain from the retina becomes gradually large, however, when the size of the figure is changed by the foregoing control, the size of the image becomes constant, and the increase of the amount of information sent to the brain from the retina can be suppressed. Incidentally, even if the size of the figure is controlled as described above, since the imaging adjustment functions can be operated to focus the eye on the figure, the effect of the vision restoration is not damaged.

Further, the display control part 42 controls also the color of the figure displayed on the target 12 and the color of the background of the figure. Data concerning the colors of the figure and the background of the figure are also stored in the storage device 43 previously, and the display control part 42 acquires the data relating to the color based on the control information inputted from the input device 34. In this case, when the color of the figure is made one of red, green and blue, and the color of the background of the figure is made black, that is, when the figure with the color of red, green or blue is displayed on the black display screen, it becomes easy for the user to concentrate on the figure. This is because photoreceptors in the retina of the human eye include cones having absorption characteristics to light of respective wavelengths of three kinds of colors of red, green and blue and rods to discriminate between light and darkness, and from the characteristics of the photoreceptors, the red, green or blue figure is easy to see. Besides, by making the background black, the discrimination of the figure can be made easier, and it becomes further easy for the user to concentrate on the figure.

Since the distance between the lens 100 and the figure is represented by the distance between the target 12 and the eyepiece part 10, the display control part 42 of the eyesight improving device of this embodiment controls the size of the figure in proportion to the distance between the target 12 and the eyepiece part 10.

The eyesight improving device of the embodiment, described above, requires about 550 to 1050 mm for the depth of the far point. This length is rather large. Then, it is preferable that the eyepiece part includes a convex lens, the depth is made small by forming a virtual image, and the apparatus is miniaturized.

EXAMPLE

Hereinafter, results of a vision improvement test carried out using the eyesight improving device of the embodiment will be described.

The eyesight improving device of the embodiment was used, and the following vision restoration training was carried out for 15 people in their teens, 23 people in their twenties, 25 people in their thirties, 14 people in their forties, and 16 people in their fifties.

Content of Training

The target 12 is reciprocated 15 times at a speed of 250 mm/second between a position where the distance between the eyepiece part 10 and the target 12 is 20 cm and a position where the distance is 65 cm, and the user focuses the eye on a white disk-shaped figure against the black background. The size of the figure is 80 mm in diameter at the far point (distance of 65 cm from the eyepiece part 10), and 24.6 mm in diameter at the near point (distance of 20 cm from the eyepiece part 10), and is linearly contracted or enlarged according to the distance from the eyepiece part 10.

Figure 9:
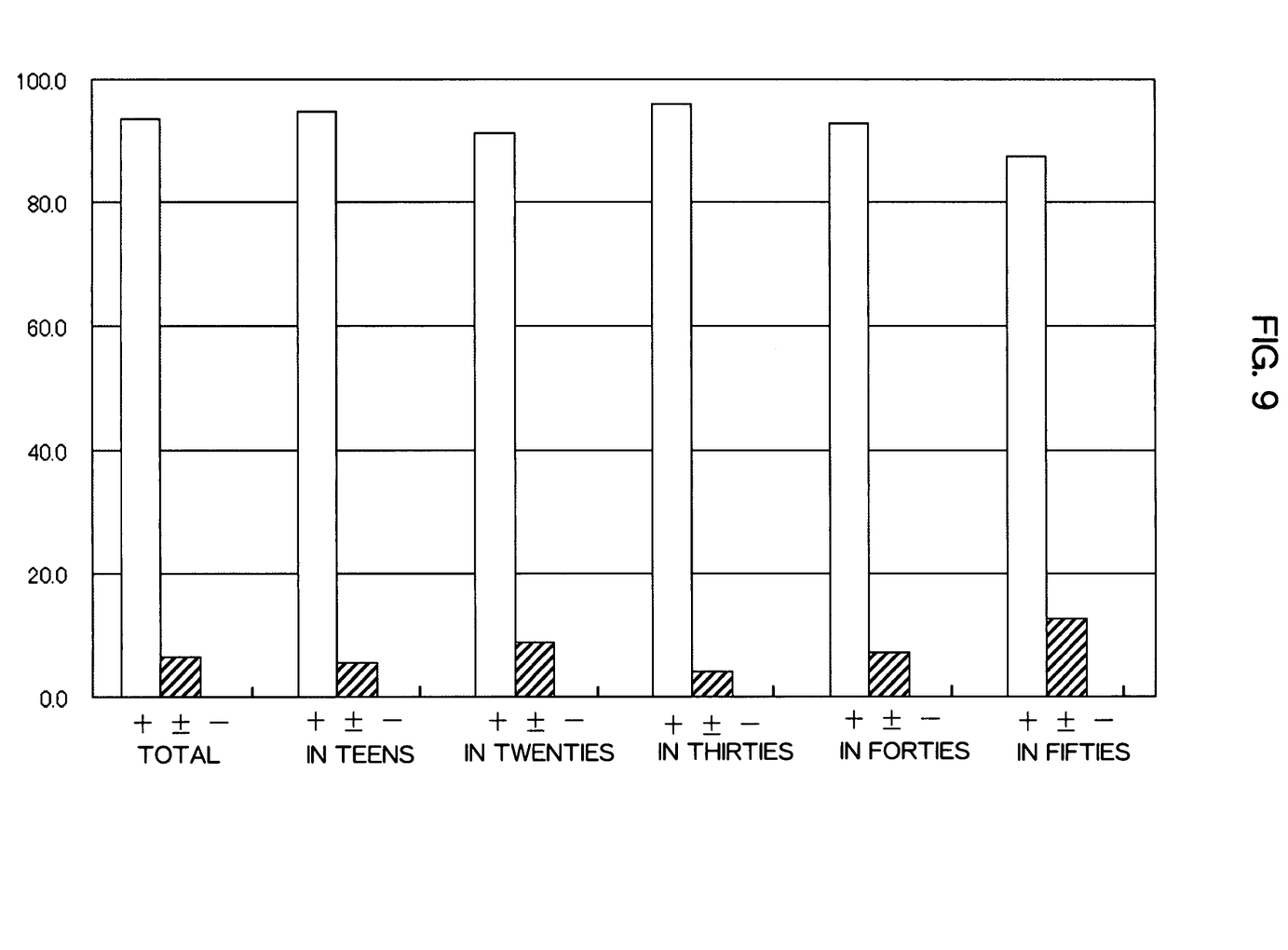
FIG. 9 is a view showing measurement results of visual acuity.

The visual acuity of each of the test subjects was determined in such a manner that with respect to test items of nine kinds in total, that is, three kinds of test items of 100%, 25% and 6% (the numeral denotes the density of a symbol) in LogMAR near distance eyesight test charts (Nippon Tenganyaku Kenkyusho), and six kinds of test items (each includes five characters and font sizes of 14 to 1) of numerals, lowercase alphabet, capital alphabet, Hiragana, Katakana, and Chinese character in character discriminant tables, in the case where a percentage of correct answers exceeded 50% at each stage of indexes of visual acuity, the person was regarded as passing the visual acuity stage (visual acuity of the person), and in the case where it was 50% or less, the visual acuity of the person was determined to be one stage below. Based on this reference, the visual acuity of each of the test subjects before and after the training was measured. Measurement results are shown in FIG. 9. In FIG. 9, synthesis "+" indicates a case where with respect to the nine kinds of test items, the number of items in which the visual acuity after the training is improved as compared with the visual acuity before the training is larger than the number of items in which it is lowered, synthesis "±" indicates a case where the visual acuity after the training is equal to the visual acuity before the training (the number of items of improvement is equal to the number of items of lowering), and synthesis "−" indicates a case where the number of items in which the visual acuity after the training is improved as compared with the visual acuity before the training is smaller than the number of items in which it is lowered.

As shown in FIG. 9, in the test subjects of the respective ages, persons with the synthesis "+" exceeded 90%, and persons with the synthesis "±" was less than 10%. Persons with the synthesis "−" did not exist. From the results, it is proved that when the training is performed using the eyesight improving device of this embodiment, the great vision improvement effect can be obtained.

Figure 4:
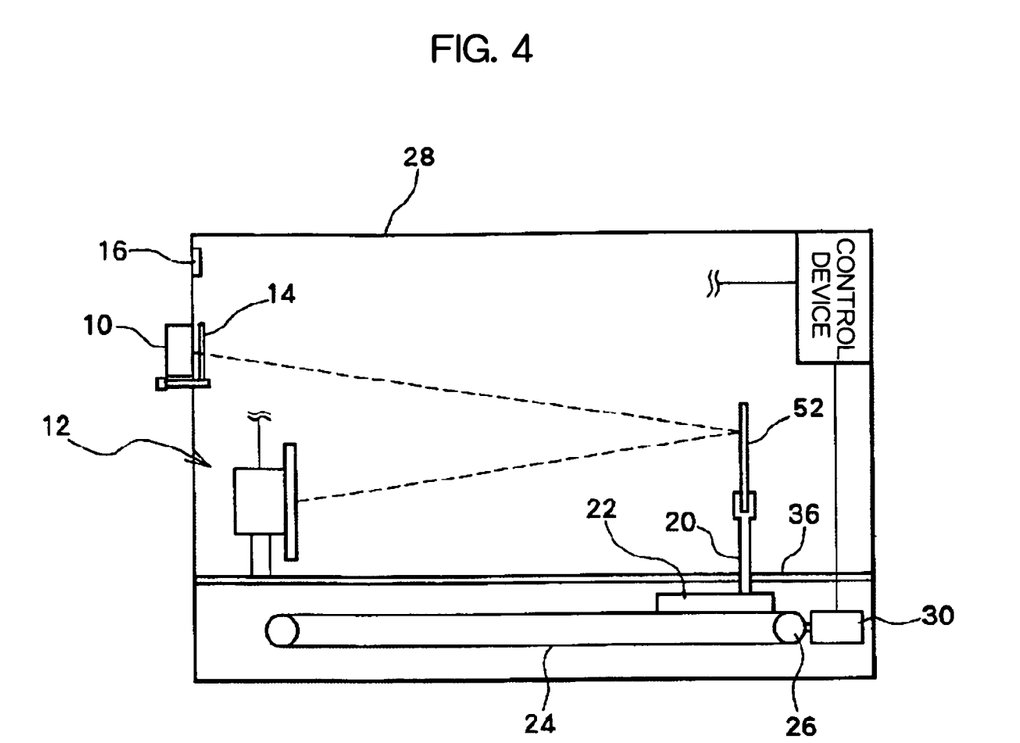
FIG. 4 is a sectional view of another embodiment of the eyesight improving device shown in FIG. 1.

FIG. 4 shows a sectional view of another embodiment of an eyesight improving device of the invention, and the same components as those of FIG. 2*a* are denoted by the same reference signs. In FIG. 4, a surface of a target 12 on which a figure is displayed is directed in the same direction as an eyepiece part 10, and reflecting device 52, such as a plane mirror, facing the target 12 and the eyepiece part 10 is provided. The reflecting device 52 is fixed to a pedestal 22 by suitable support device 20 such as a post. The reflecting device 52 fixed to the pedestal 22 is moved by transport device 24 at a suitable speed between two specified points. The pedestal 22, the transport device 24 and a motor 30 constitute reflecting device movement device of the invention.

As indicated by a broken line in FIG. 4, light from the target 12 is reflected by the reflecting device 52 and is incident on the eyepiece part 10. Accordingly, the user indirectly visually sees a figure of the target 12 through the reflecting device 52 from the eyepiece part 10. Besides, the passing distance of light which is emitted from the target 12, is reflected by the reflecting device 52 and reaches the eyepiece part 10, that is, the distance to the target 12 when the user sees it from the eyepiece part 10 can be adjusted by moving the position of the reflecting device 52. Accordingly, as the two specified points between which the reflecting device 42 is moved, setting can be made such that the passing distances of light become the distances of the far point and the near point. The actual distance between the eyepiece part 10 and the reflecting device 52 at that time can be made shorter than the passing distance of the light since the light is reflected by the reflecting device 52. By the structure as stated above, with respect to the distance to the target 12 seen by the user from the eyepiece part 10, while the specified far point is secured, the depth of the eyesight improving device is made small, and the miniaturization of the apparatus can be realized. Incidentally, the position of the reflecting device 52 can be detected by the same structure as the position control part 48 shown in FIG. 2b. Thus, by the same structure as the control device 32 shown in FIG. 2b, it is possible to perform the control to change the size of the figure displayed on the target 12 in proportion to the passing distance of light. Besides, the control of the colors of the figure and the background of the figure can also be similarly performed.

Figure 5A:
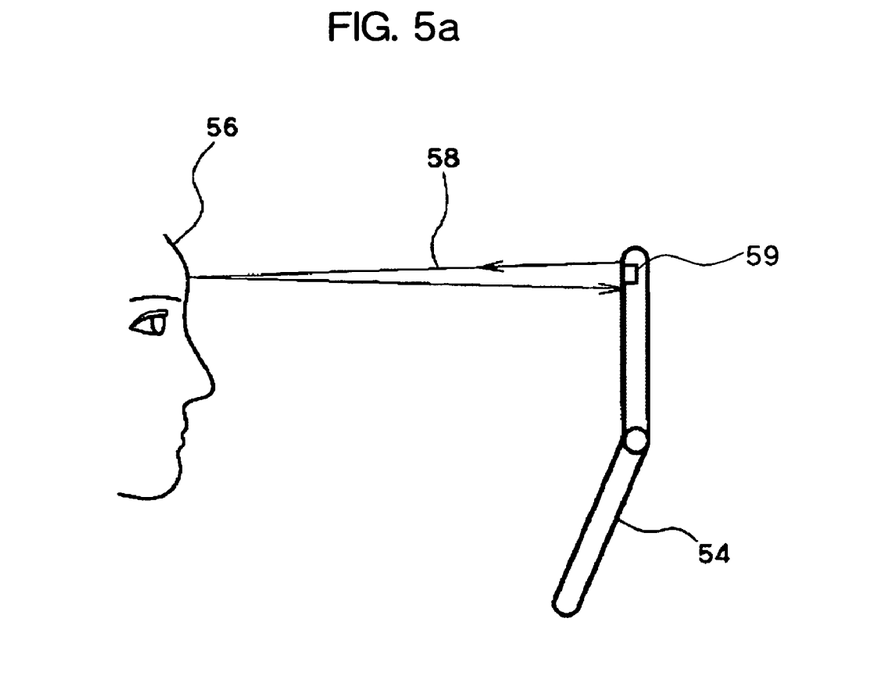
FIG. 5a is a view showing a structure of still another embodiment of an eyesight improving device of the invention.

FIG. 5a is structural view of a still another embodiment of an eyesight improving device of the invention. In FIG. 5a, instead of the target 12, a figure is displayed on electric display, such as a liquid crystal display device, provided in a cellular phone 54. The user takes the cellular phone 54 in his/her hand, reciprocates the figure at a suitable speed by bending and stretching the arm, sees the figure while focusing the eye thereon, so that vision restoration training is performed.

The cellular phone 54 includes distance measurement device for measuring the distance from a user 56. As the distance measurement device, it is possible to adopt, for example, a structure in which a light emitting element and a light receiving element are incorporated in the cellular phone 54, and as shown in FIG. 5a, a light 58 emitted from the light emitting element and reflected by the face of the user 56 is detected by the light receiving element, a time from the emission of the light from the light emitting element to the detection of the reflected light by the light receiving element is measured and the distance is measured, or a structure in which the cellular phone 54 is made to have a camera function 59, only a specific portion is extracted from the object screen and is stored, and when the distance is changed, the distance is calculated based on the ratio of the length of the specific portion. However, the distance measurement device is not limited to these, and as long as it can be incorporated in the cellular phone 54, the limitation is not made. In this embodiment, the structure is made such that the size of the figure displayed on the electric display is changed in proportion to the distance between the cellular phone 54 and the user 56, which is measured by the distance measurement device. By this, similarly to the foregoing embodiment, it is possible to realize the eyesight improving device in which the user can easily focus the eye on the displayed figure and which is easy to use.

Figure 5B:
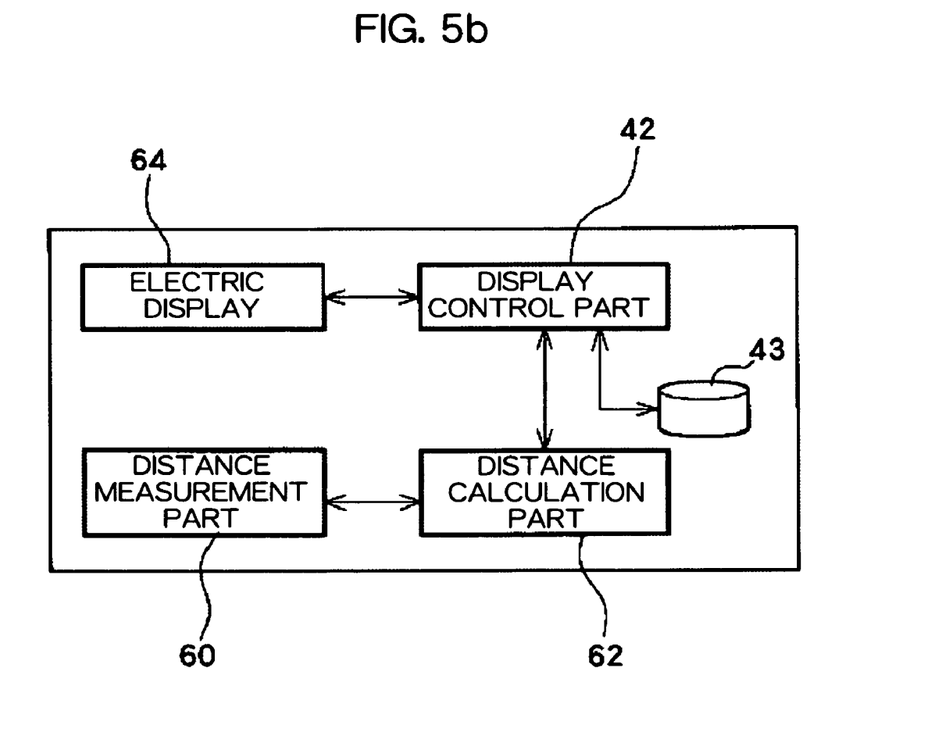
FIG. 5b is a view showing a structure of still another embodiment of an eyesight improving device of the invention.

FIG. 5b is block diagram of the structure for realizing the embodiment shown in FIG. 5a. Incidentally, in FIG. 5b, a portion to realize the cellular phone function is omitted. In FIG. 5b, the distance between the cellular phone 54 and the user 56 is measured by a distance measurement part 60 constructed of the foregoing camera function 59 and the like, the output of the distance measurement part 60 is inputted to a distance calculation part 62, and the distance is calculated. Here, the distance measurement part 60 and the distance calculation part 62 constitute distance measurement device of the invention. Distance data calculated by the distance calculation part 62 is inputted to a display control part 42. The display control part 42 corresponds to the display control device of the invention. The display control part 42 performs the control such that based on the inputted distance data, the size of the figure displayed on the electric display 64 is changed in proportion to the distance between the cellular phone 54 and the user 56. At this time, similarly to the case of FIG. 2b, the figure displayed on the electric display 64 is selected by the display control part 42 from figure data stored in the storage device 43. Besides, the colors of the figure and the background of the figure can also be controlled similarly to the case of FIG. 2b.

Incidentally, in this embodiment, although the example in which the eyesight improving device is realized by the cellular phone has been described, limitation to the cellular phone is not made. When the structure shown in FIG. 5b is incorporated in something which is carried by the user and can display a suitable figure, for example, a PDA (Personal Digital Assistance), the eyesight improving device of the embodiment can be realized.

Figure 7A:
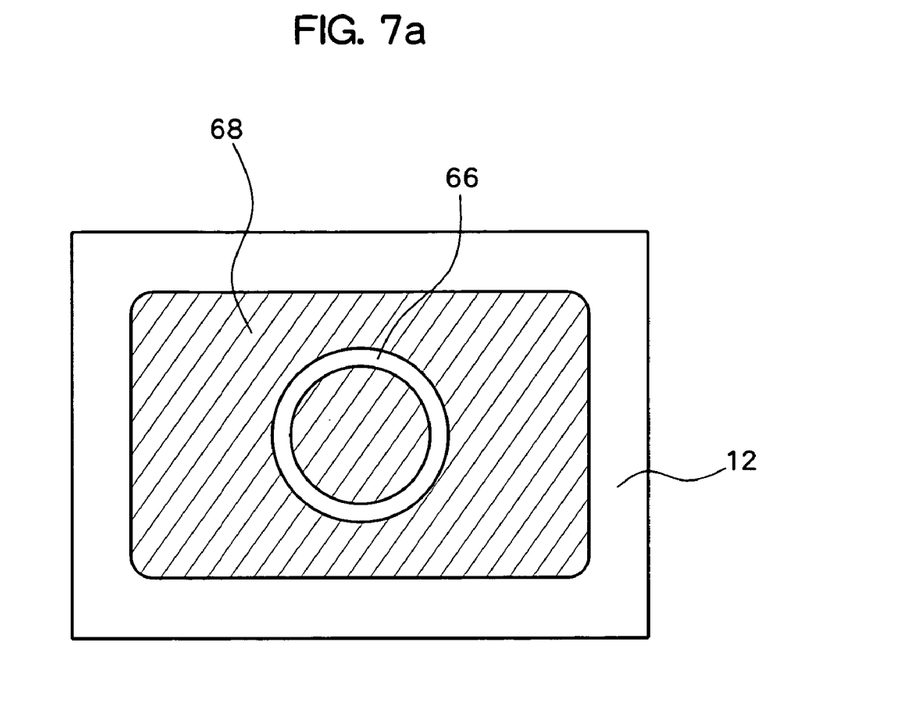
FIG. 7a is a view showing a structure of still another embodiment of an eyesight improving device of the invention.
Figure 7B:
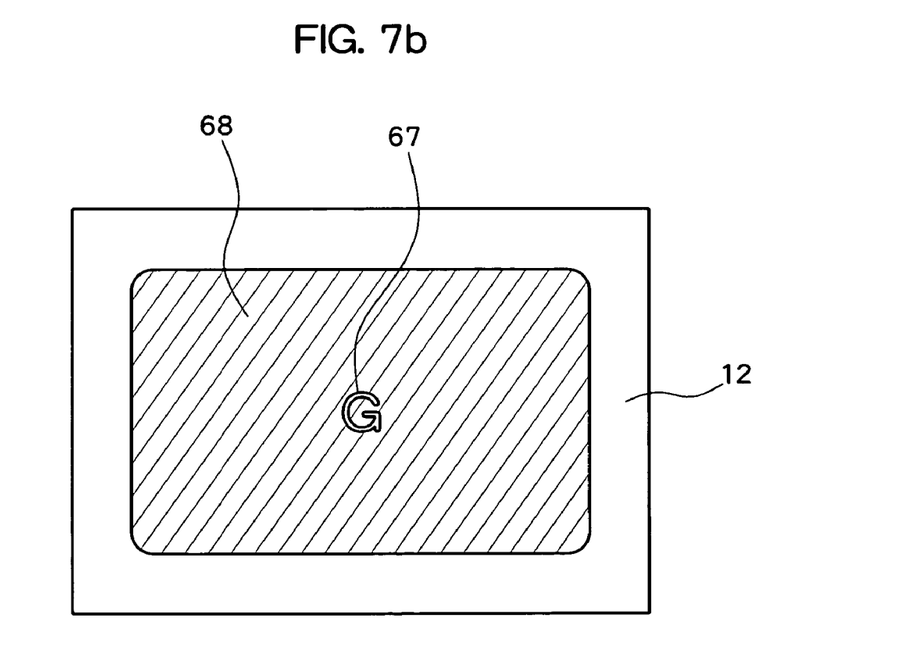
FIG. 7b is a view showing a structure of still another embodiment of an eyesight improving device of the invention.

FIGS. 7a and 7b are structural views of still another embodiment of an eyesight improving device of the invention. In FIG. 7a, a figure 66 in this embodiment is displayed on a target 12. The shape of the figure 66 is a round shape with a hole at the center portion as shown in FIG. 7a, that is, a ring shape. Besides, on a screen 68 of the target 12 displaying the FIG. 66, the background of the figure 66 is displayed to be black.

Figure 8:
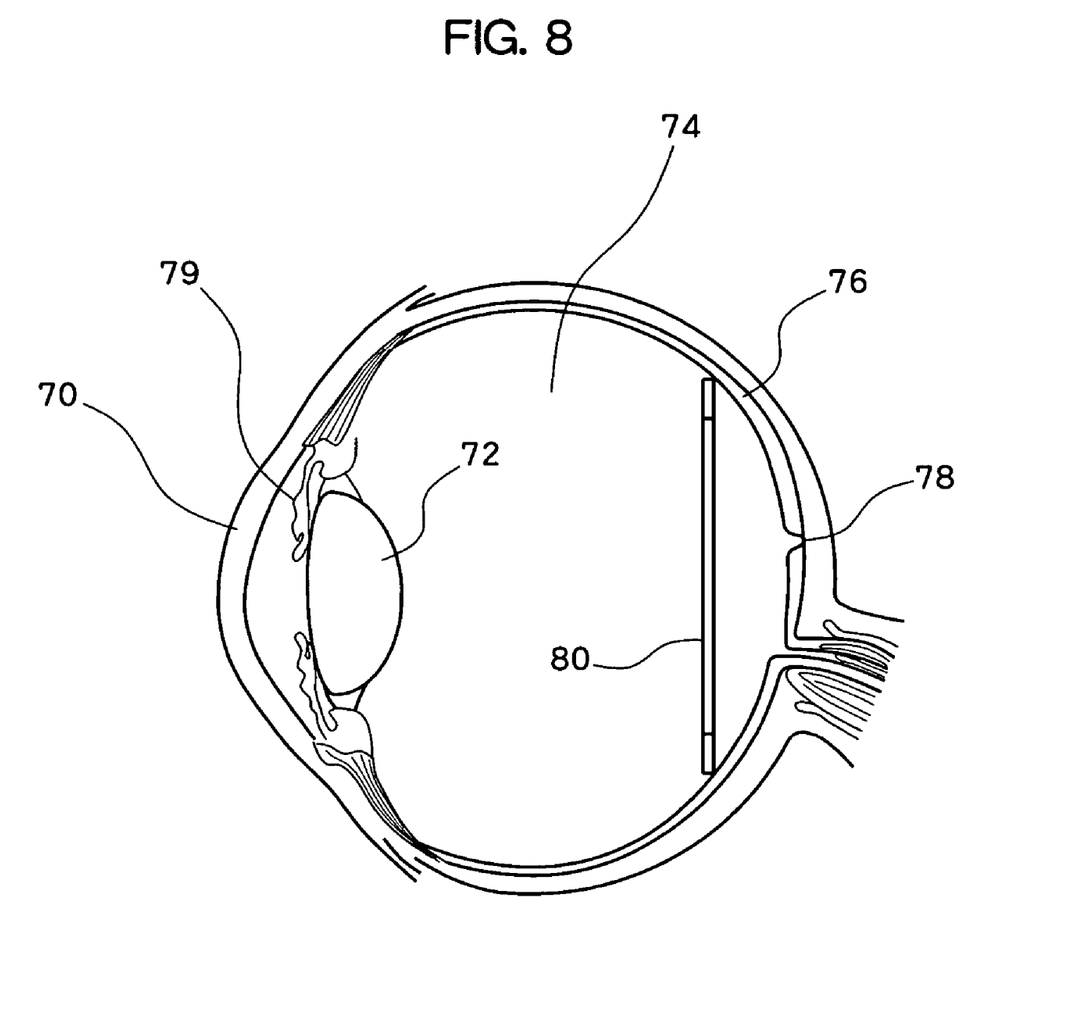
FIG. 8 is a partial sectional view of a detailed structure of a human eye.

FIG. 8 is a partial sectional view of a detailed structure of a human eye. In FIG. 8, light entering the eye forms an image of an object on a retina 76 through a cornea 70, a crystalline lens 72 and a vitreous body 74. A fovea centralis 78 where the visual acuity is best exists almost at the center of the retina 76. Besides, in order to more clearly sense the object, a pupil diameter is adjusted by an iris 79 positioned at the front of the crystalline lens 72.

In the case where the ring-shaped figure 66 shown in FIG. 7a is seen by the human eye, an image 80 is formed approximately at a position shown in FIG. 8. As described above, the figure 66 is ring-shaped and has the shape in which the circular hole is bored in the center portion. Thus, the image 80 of the figure 66 is not formed in the region of the fovea centralis 78 of the eye, stimulation to the fovea centralis 78 is suppressed, and the image 80 is sensed by retina stimulation around the fovea centralis 78. By this, particularly for an elderly user, that is, the user whose presbyopia is advanced, it becomes easy to see the figure 66, and it becomes easy to concentrate on seeing the figure 66. Thus, the ocular imaging adjustment functions of the ciliary muscle 102 and the like can be effectively operated, and the imaging adjustment functions can be further improved.

Although the figure 66 shown in FIG. 7a is a single ring, it is preferable that this is made a double ring. When the double ring is adopted, it becomes easy to make a judgment as to whether the eye is focused on the figure 66, and it becomes possible to focus the eye on the figure 66 and to operate the ocular imaging adjustment functions more effectively. In case the eye is not focused on the figure 66, the ocular imaging adjustment functions of the ciliary muscle 102 and the like can not be sufficiently operated.

Incidentally, the size of the figure 66 is not particularly limited as long as the size is such that the retina around the fovea centralis 78 can be stimulated.

The ring-shaped figure 66 of FIG. 7*a* described above is suitable for an elderly person whose problem is mainly presbyopia. On the other hand, for a young person, that is, a user whose problem is myopia, there is also a case where it is easier to concentrate on the light stimulating the fovea centralis 78 of the eye. FIG. 7*b* shows an example of a figure suitable for stimulating the fovea centralis 78 of the eye. In FIG. 7*b*, in a target 12, a figure 67 with a capital G in alphabet is displayed at almost the center of a screen 68 against the black background. It is preferable that the size of this figure 67 is such that when the distance from the eyepiece part 10 to the figure 67 (the screen 68 of the target 12) is 25 cm, the maximum diameter is 1 cm or less. When such a size is adopted, almost all light incident on the eye from the figure 67 can stimulate the fovea centralis 78. When the FIG. 67 is made the capital G in the alphabet as shown in FIG. 7*b*, by the horizontal line of "T" at the center part of G, it becomes easy to make a judgment as to whether the eye is focused, and it becomes possible to more effectively operate the ocular imaging adjustment functions. Incidentally, the figure 67 is not limited to the capital G in the alphabet, and for example, a disk with the above size may be adopted.

It is preferable that the figure 66 and 67 as described above are made white and the background is made black as stated above. By this, the stimulation to the eye by the figures 66 and 67 becomes intense, and the user can concentrate on and more easily see the figures 66 and 67.

INDUSTRIAL APPLICABILITY

As described above, according to the invention, since the size of the figure is changed in proportion to the distance between the target and the eyepiece part, when the target is moved, it becomes easy to focus the eye on the figure, and the eyesight improving device easy to use can be provided.

Besides, when the eyesight improving device is used, binocular vision and monocular vision can be easily selected by the blocking device.

Besides, by using the electric display unit as the target, the number of selectable figures can be increased, and the clearer figure can be provided.

Besides, by moving the target by the driving device, the movement of the target is facilitated, and the target can be moved at an accurate speed, and accordingly, the vision improvement effect can be more raised. At that time, since the movement speed of the target can be stepwise or continuously changed, the movement speed most suitable for the user can be easily set.

Besides, by using the convex lens in the eyepiece part, or by providing the reflecting device between the target and the eyepiece part, the eyesight improving device can be miniaturized.

Besides, by incorporating the eyesight improving device of the invention in the cellular phone or the like, the small and simple eyesight improving device can be realized.

Besides, by properly using the figure such as the ring shape or the capital G in the small alphabet according to the condition of the user such as the age, the suitable vision improvement training can be carried out.

The invention claimed is:

1. An eyesight improving device comprising:
   an eyepiece part;
   a target visually seen from the eyepiece part and capable of displaying a suitable figure;
   a target movement device which moves the target at a suitable speed between a far point and a near point each of which is positioned at a specified distance from the eyepiece part; and
   a display control device which changes a size of the figure displayed on the target continuously while the target moves in proportion to a distance between the target and the eyepiece part, so that a size of an image formed on a retina of a user's eye is kept constant while the target moves.

2. An eyesight improving device according to claim 1, wherein two such eyepiece parts are provided, and a blocking device which blocks visual identification of the target is provided for each of the eyepiece parts.

3. An eyesight improving device according to claim 1, wherein the target includes an electric display which displays the figure visually seen from the eyepiece part.

4. An eyesight improving device according to claim 1, wherein the target movement device moves the target by a driving device.

5. An eyesight improving device according to claim 4, wherein the driving device can change a movement speed of the target stepwise.

6. An eyesight improving device according to claim 4, wherein the driving device can change a movement speed of the target continuously.

7. An eyesight improving device according to claim 1, wherein the eyepiece part includes a convex lens.

8. An eyesight improving device according to claim 1, wherein:
   the target is directed in a same direction as the eyepiece part;
   a reflecting device which faces the target and the eyepiece part and a reflecting device movement device which moves the reflecting device at a suitable speed between two specified points, instead of the target movement device, are provided; and
   light from the target is reflected by the reflecting device and is incident on the eyepiece part.

9. An eyesight improving device, comprising:
   an electric display which can display a suitable figure;
   a distance measurement device which measures a distance from a user; and
   a display control device which changes a size of the figure displayed on the electric display continuously while the electric display moves in proportion to the distance from the user, so that a size of an image formed on a retina of a user's eye is kept constant while the electric display moves.

10. An eyesight improving device according to claim 1, wherein the figure is displayed in one of red, green and blue, and a background of the figure is black.

11. An eyesight improving device according to claim 1, wherein the figure is ring-shaped.

12. An eyesight improving device according to claim 1, wherein the figure has such a size that when a distance from the eyepiece part is 25 cm, a maximum diameter is 1 cm or less.

13. An eyesight improving device according to claim 12, wherein the figure has a shape of a capital G in an alphabet.

14. An eyesight improving device according to claim 11, wherein the figure is displayed in white, and a background of the figure is black.

15. An eye sight improving device according to claim 1, wherein the sight improving device does not include an optical magnification or reduction device.

* * * * *